United States Patent
Neoh et al.

(10) Patent No.: US 8,265,352 B1
(45) Date of Patent: Sep. 11, 2012

(54) PHOTOGRAPHIC FINGERPRINT COLLECTION AND IMAGING SYSTEM

(75) Inventors: Kenneth C. Neoh, Grant Town, WV (US); John Hurt, Lumberport, WV (US)

(73) Assignee: Azimuth, Inc., Morgantown, WV (US)

( * ) Notice: Subject to any disclaimer, the term of this patent is extended or adjusted under 35 U.S.C. 154(b) by 740 days.

(21) Appl. No.: 12/057,997

(22) Filed: Mar. 28, 2008

Related U.S. Application Data

(60) Provisional application No. 60/908,509, filed on Mar. 28, 2007.

(51) Int. Cl.
*G06K 9/00* (2006.01)

(52) U.S. Cl. ........ 382/124; 382/115; 382/116; 382/125; 382/126; 382/127

(58) Field of Classification Search .......... 382/115–116, 382/124–127
See application file for complete search history.

(56) References Cited

U.S. PATENT DOCUMENTS

| | | | | |
|---|---|---|---|---|
| 3,564,266 A | * | 2/1971 | Klotz, Jr. .......................... | 377/19 |
| 4,947,261 A | * | 8/1990 | Ishikawa et al. ............. | 358/473 |
| 5,508,504 A | * | 4/1996 | Dvorkis et al. .......... | 235/472.03 |
| 5,528,288 A | * | 6/1996 | Sandor et al. .................... | 348/97 |
| 5,576,527 A | * | 11/1996 | Sawanobori .................... | 235/455 |
| 5,999,666 A | * | 12/1999 | Gobeli et al. .................. | 382/313 |
| 6,033,087 A | * | 3/2000 | Shozo et al. .................. | 362/244 |
| 6,212,290 B1 | * | 4/2001 | Gagne et al. .................. | 382/125 |
| 6,481,628 B2 | * | 11/2002 | Liou et al. ................ | 235/472.03 |
| 6,485,981 B1 | * | 11/2002 | Fernandez ....................... | 436/71 |
| 7,729,509 B2 | * | 6/2010 | Alasia et al. ................... | 382/100 |
| 7,978,259 B2 | * | 7/2011 | Matsuo et al. ................ | 348/370 |
| 2004/0119975 A1 | * | 6/2004 | Ostler et al. .................. | 356/318 |
| 2004/0240713 A1 | * | 12/2004 | Hata ............................. | 382/124 |
| 2006/0072314 A1 | * | 4/2006 | Rains ............................. | 362/231 |
| 2006/0125918 A1 | * | 6/2006 | Sutton ........................... | 348/148 |
| 2006/0218987 A1 | * | 10/2006 | Campman ...................... | 73/23.2 |
| 2007/0098391 A1 | * | 5/2007 | Howard et al. ................ | 396/155 |
| 2008/0204551 A1 | * | 8/2008 | O'Connell et al. ............. | 348/79 |

* cited by examiner

*Primary Examiner* — Jayesh A Patel
(74) *Attorney, Agent, or Firm* — Dinsmore & Shohl LLP; Monika J. Hussell

(57) ABSTRACT

The present invention regards a system comprised of a camera lens, a sensor, a light source and a structure for directly collecting (imaging) latent fingerprints from surfaces, either naturally or with a reagent to fluoresce, and suitable for use in military tactical environments. The present invention is intended to be used with a portable computer, having software capable of receiving, storing and processing images collected by the device of the present invention.

12 Claims, 18 Drawing Sheets

PHOTOGRAPHIC FINGERPRINT COLLECTION AND IMAGING SYSTEM

BACKGROUND OF THE INVENTION

The present invention regards a fingerprint collection system comprising a camera lens, a sensor, a light source and a cylindrical structure, for directly collecting (imaging) fingerprints from surfaces, either naturally or with a reagent to fluoresce, and is suitable for use in military tactical and practical investigative environments. The present invention is intended to be used with a portable computer, having software capable of receiving, storing and processing images collected by the device of the present invention.

The first challenge to collecting latent fingerprints is the ability of identifying them on objects. Latent fingerprints are difficult to observe and collect, because typically only a tenth of a milligram of material is deposited on the surface. About 99% of a latent fingerprint is water, which soon evaporates to leave behind about a microgram of residue. About half of this residue is inorganic material, such as sodium chloride (ordinary salt), potassium chloride, calcium salts, etc. The other half is a complex mixture of organic compounds such as lipids, amino acids, vitamins, etc.

The fluorescence frequency of a fingerprint can be regarded as the "signature" of the organic compounds that constitute the fingerprint so that it can be used for its identification and separation from the background or surface fluorescence. To make the fingerprint fluoresce, one of these organic compounds must be stimulated to glow. In some cases the salts or inorganic compounds will fluoresce naturally (known as primary or auto fluorescence), which will allow an image of the fingerprint to be captured. Fingerprints can also be made to fluoresce when treated with chemicals capable of fluorescing (known as secondary fluorescence). Furthermore, because latent fingerprints consist of very little material, a luminescence strong enough to be visible to the naked eye requires a very intense illumination of the correct frequency.

Because additional equipment and training are required to dust latent prints with florescent powders and capture images of them using existing technologies, and then physically lift the print, applicant endeavored to develop an all-in-one device and method that could be used by individuals without specialized training. Furthermore, currently fingerprints that have been lifted from a surface have to be scanned into an electronic format, and ingested/enrolled into a database. The probability of recovering good fingerprint images is dependent on the environment (e.g., temperature, humidity, and exposure to sun light), how the object is handled, and the environmental conditions encountered following the recovery.

In addition to the traditional techniques, which can require specialized training and equipment, lasers and narrow frequency band lighting techniques have been used in the direct collection of fingerprints from objects. However, these techniques can require expensive digital cameras because of specialized Charged Coupled Devices (CCD), lenses, and optical filters that are sensitive to the frequency of light used to illuminate the fingerprint.

Presently alternative fingerprint collection techniques being researched such as micro-X-ray fluorescence (MXRF) and infrared spectra-microscopy (FTIR-SM). These techniques are more suited for laboratory collection than in military tactical or practical investigative environments.

Digital cameras designed for photography of fingerprints include the Fujifilm Finpix S3 PRO UVIR. However, this camera is very complicated to use, expensive and requires additional lighting sources. Other digital single lens reflex (SLR) cameras could be modified for purposes of fingerprint collection, but suffer many of the same constraints as the Fujifilm S3 PRO UVIR.

Based on the complicated nature of current fingerprint detection and collection technology, there is a need for an all-in-one camera that is relatively inexpensive, simple to use, durable, portable, operates on low-power, and that accurately collects (images) fingerprints and other forensic evidence directly from surfaces.

Thus the objects of the present invention are to provide a device to increase capacity to gather fingerprint evidence; to reduce the costs of gathering fingerprint evidence by providing a device that can be used by modestly trained individuals rather than forensic experts; to enable source identification for fingerprints in a relatively short period of time; to capture decaying evidence quickly; and to directly collect fingerprint evidence from porous or rough surface.

GENERAL DESCRIPTION

The primary purpose of the system of the present invention is to collect images of visible and latent fingerprints on surfaces. The fundamental design parameters of the imaging system include its field of view (FOV), working distance, resolution, depth of field (DOF), and sensor size. FOV is the viewable area of the object under inspection and is sometimes measured in surface area imaged at the working distance and other times as angular FOV. In other words, it is the portion of the object that fills the camera sensor. The distance from the front of the lens to the object under inspection is the working distance (a constant, as it is the distance from the lens to the bottom of the structure, which when in use will rest on the surface having the fingerprint), and the minimum feature size that the system can discern is its resolution. The DOF is the maximum object depth that can be maintained entirely in focus. The active area of the camera sensor is referred to as its sensor size and is typically specified in the horizontal dimension. It is used in determining the degree of lens magnification needed to get a desired field of view. Another useful parameter is the primary magnification of the lens. It is the ratio between the sensor size and the field of view. Also bearing on image quality are three other properties: image contrast, perspective errors, and distortion. These factors are considered to determine the minimum acceptable image quality. In general, fingerprints prepared for submission to national databases for comparison must be 500 or 1000 pixels per inch 8 bit grayscale.

Using the present device, invisible fingerprints, visible prints and plastic prints can be captured without destroying the physical evidence. The device of the present invention controls the lighting, exposure, focus, field of view and depth of view (all of which are constants in accordance with the present invention), thereby maximizing the quality of the image while requiring little or no adjustment by the user. Specifically, lighting is controlled by the automated configuration or adjustment of lighting intensity (including the attenuation or ambient lighting), the light to shutter gating and duration, and the incidence angle of light (including oblique angle and backlighting).

Furthermore, the exposure can be controlled by the automated configuration of shutter speed, apertures, gating and shutter to light source, and the control of the light source(s) before and during an open-gated shutter event.

In addition, the device has the ability to apply multiple illumination profiles (intensity, spectra, angle) and also capture 'bracketed" images (taking several shots of the same subject using different camera settings).

Because the structure of the present invention is fixed in size, and provides a constant FOV, DOF, sensor size, and magnification, the structure is easy to use, the software on the associated computer can be simplified, errors are reduced, and image quality is increased. Furthermore, because the device of the present invention sets the lens to a fixed focal length, there is no need to capture a ruled scale in the image.

The device of the present invention is further designed for simplicity of operation, by having a single push button to capture the image, and a single multi-position switch to select illumination frequency (e.g., IR, white, UV). Furthermore, the form, fit, and function of the device include several advantages for its intended purpose, including the fact that it is small and light weight, and consumes only a small amount of power.

The present invention generally comprises a lens, a sensor, a light source, and a cylindrical structure to support the same. The support structure may comprise a lens support structure and a light support structure. Embodiments of the present invention are shown in the figures accompanying this written description.

DETAILED DESCRIPTION OF PREFERRED EMBODIMENTS

Figure 1:
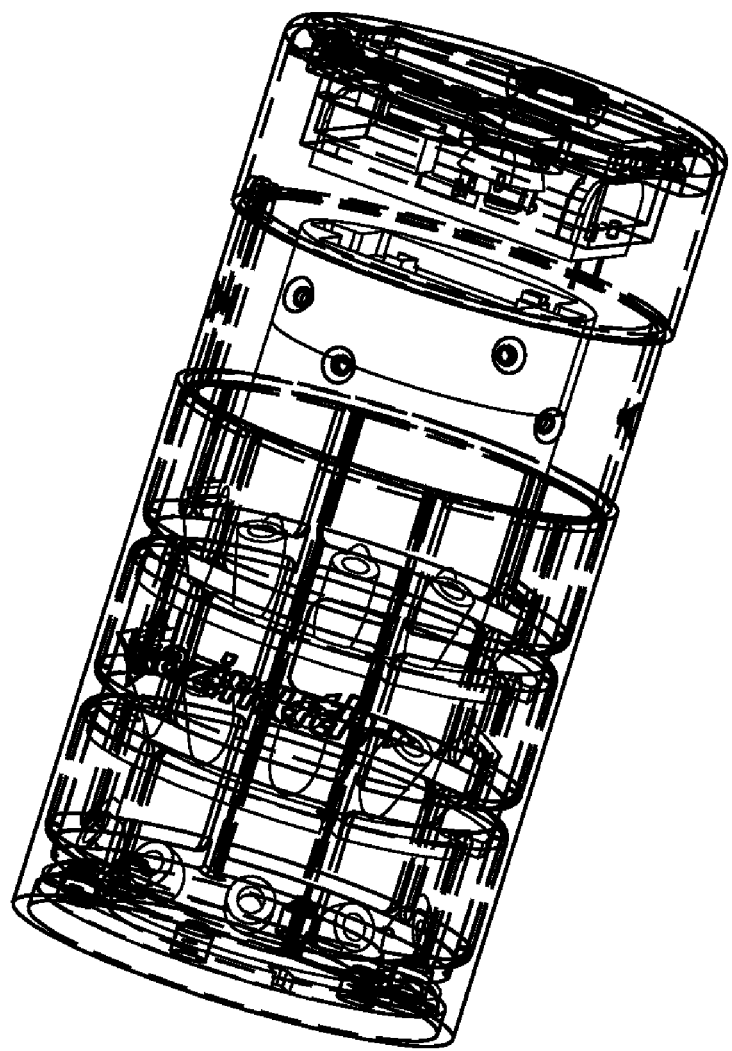
FIG. 1 is a depiction of an embodiment of the present invention.
Figure 2:
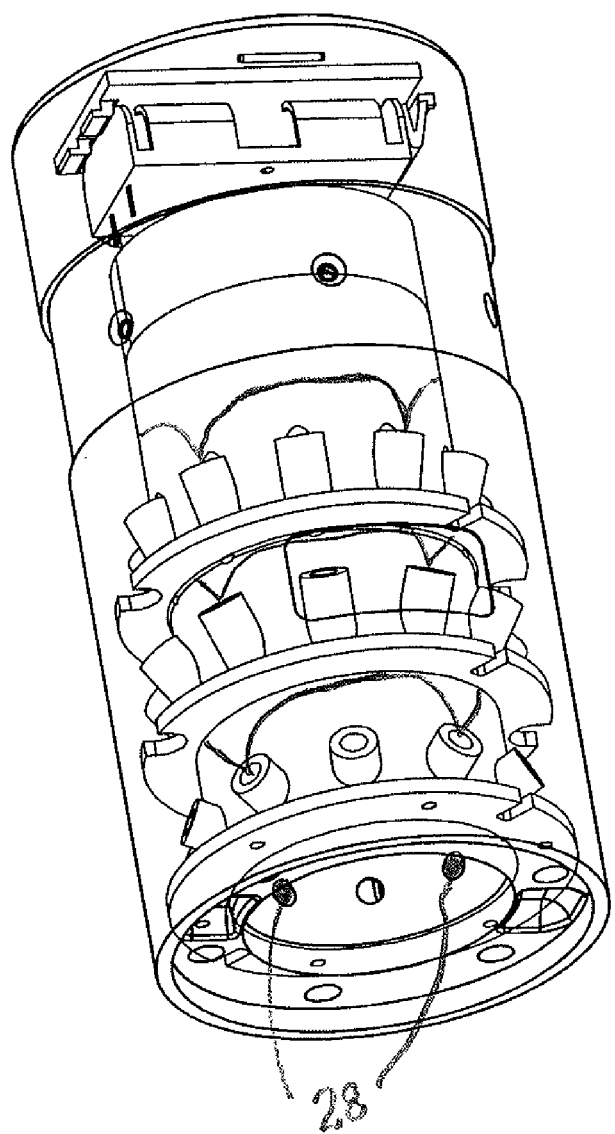
FIG. 2 is a depiction of an embodiment of the present invention.
Figure 3:
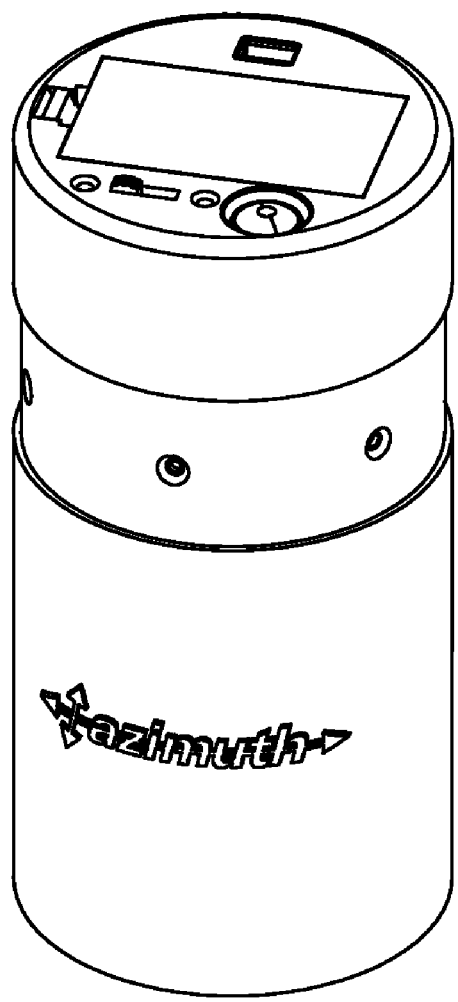
FIG. 3 is a depiction of the exterior of the present invention.
Figure 4:
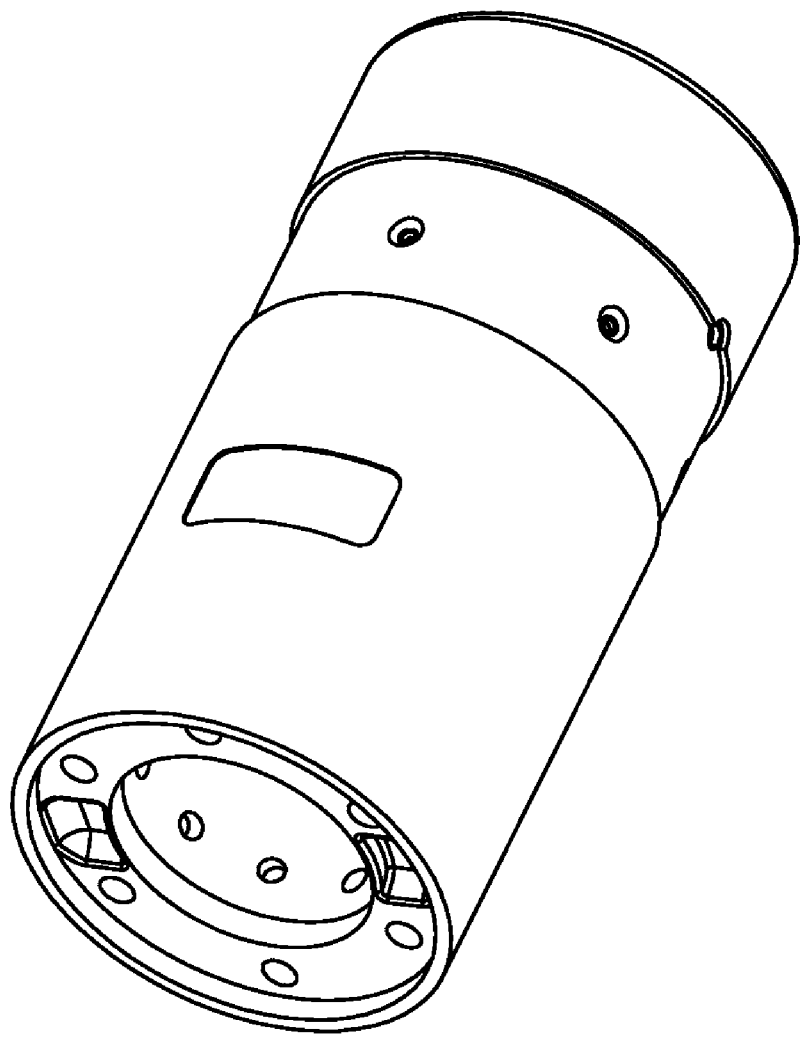
FIG. 4 is a depiction of the exterior of the present invention, from the bottom.
Figure 5:
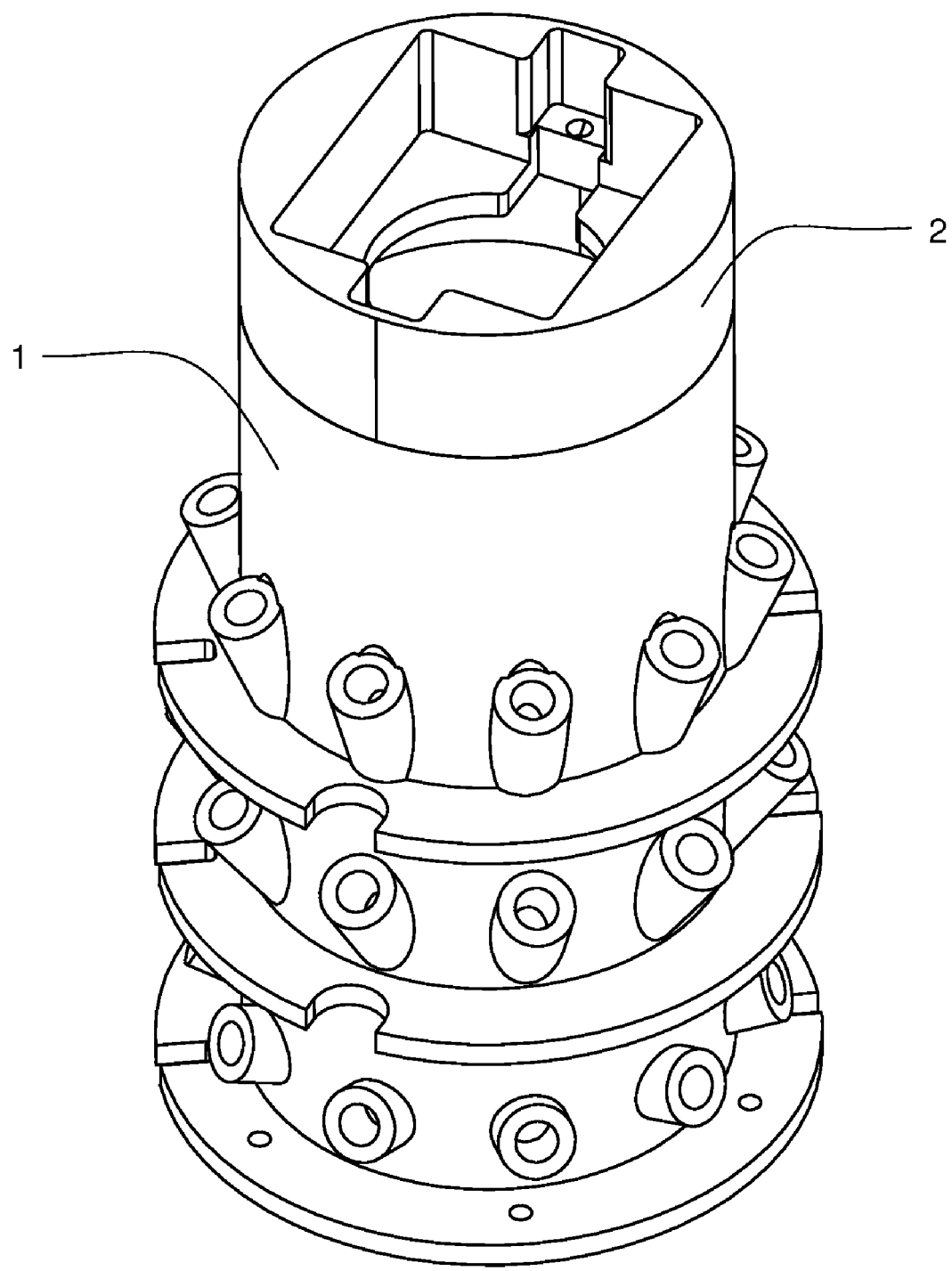
FIG. 5 is a depiction of the light support and lens support structures of the present invention.
Figure 6:
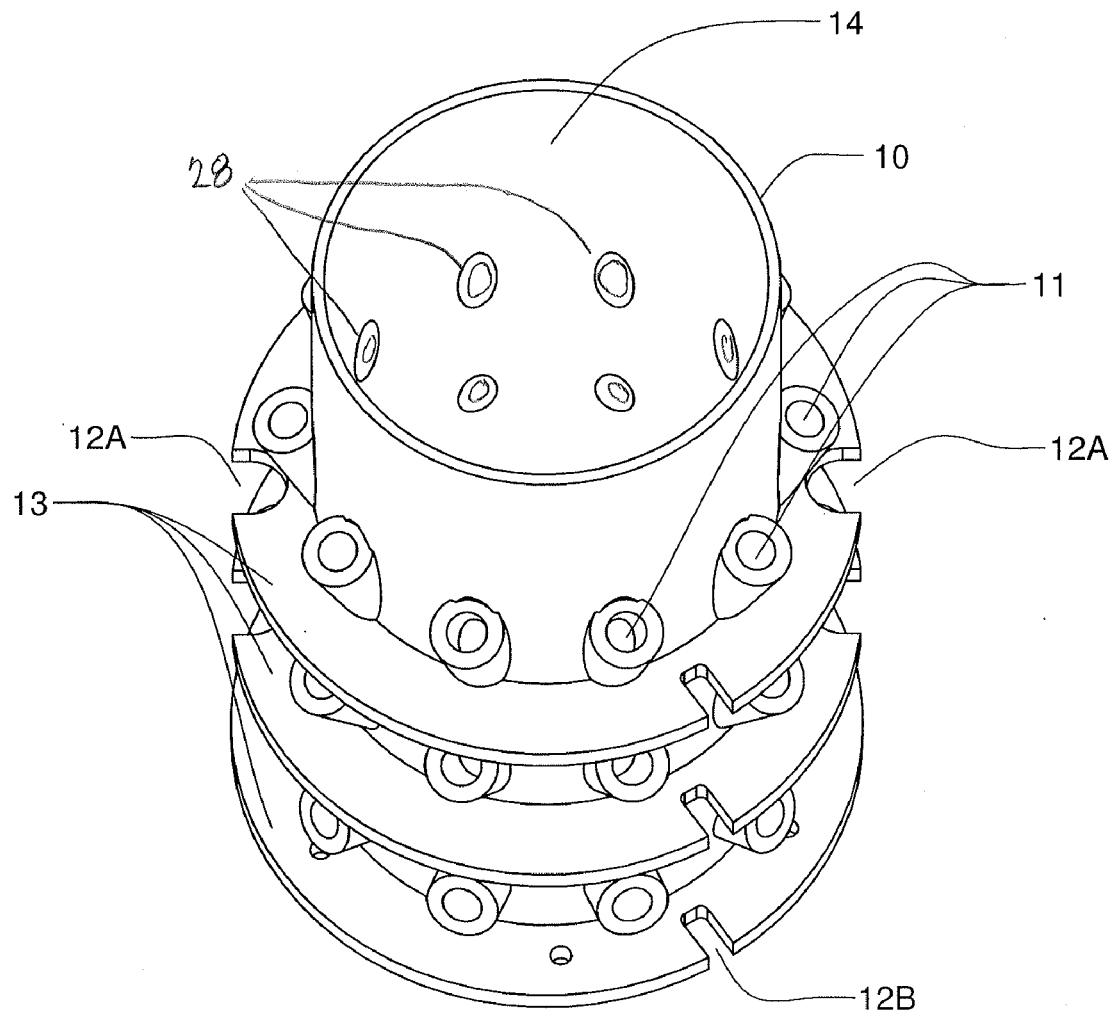
FIG. 6 is a depiction of the light support structure of the present invention.
Figure 7:
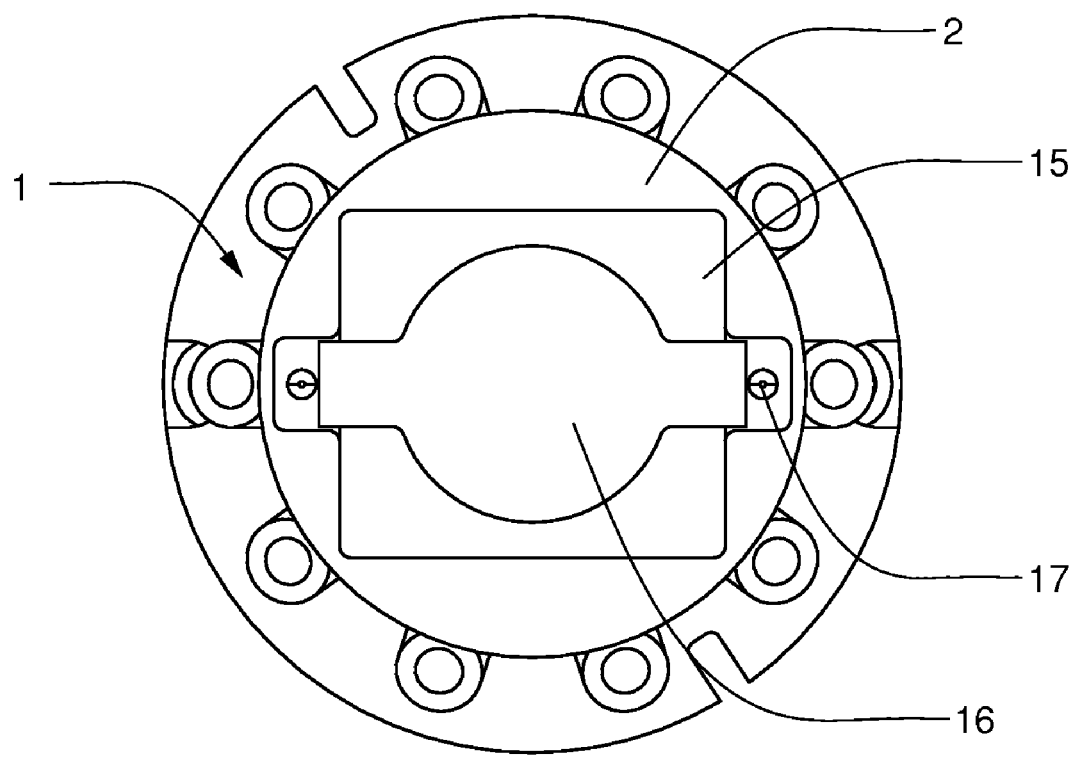
FIG. 7 is a depiction of the light support structure cap of the present invention.
Figure 8:
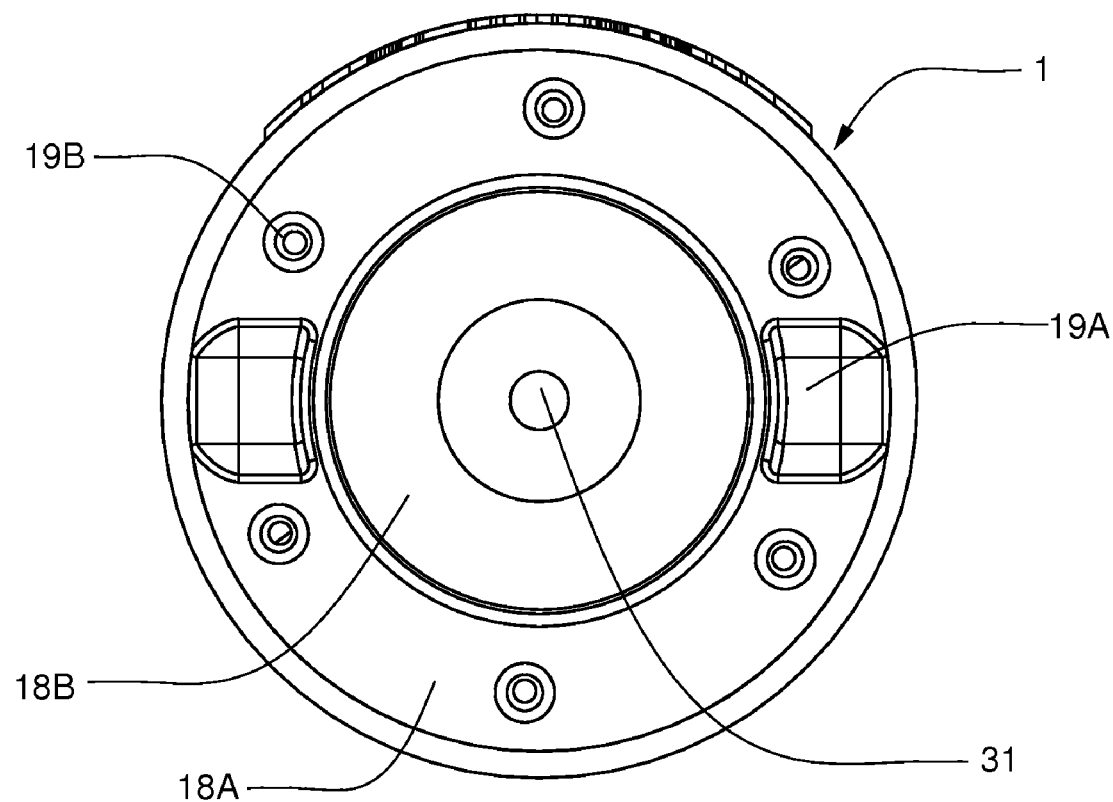
FIG. 8 is a depiction of the bottom of the light support structure of the present invention.
Figure 9:
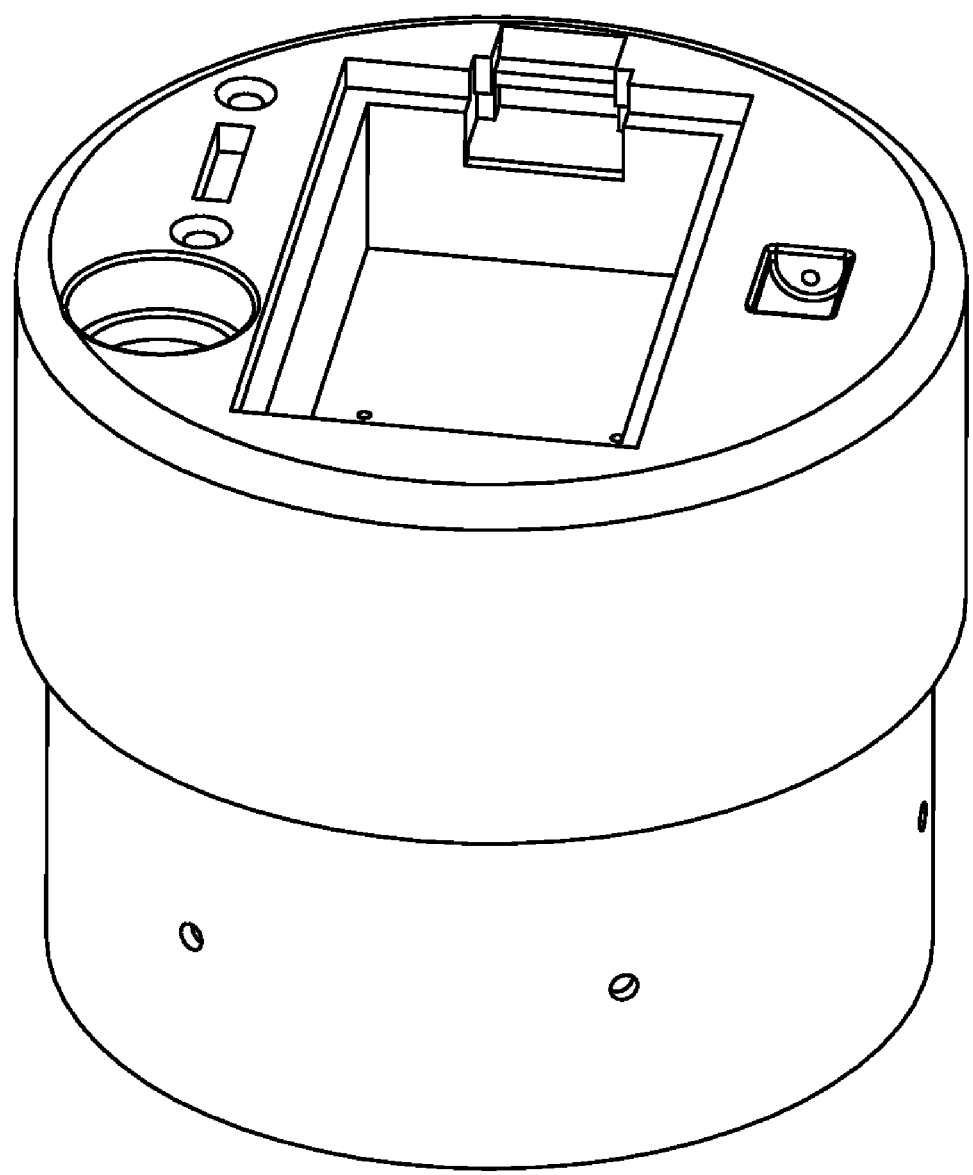
FIG. 9 is a depiction of the lens, power and control support of the present invention.
Figure 10:
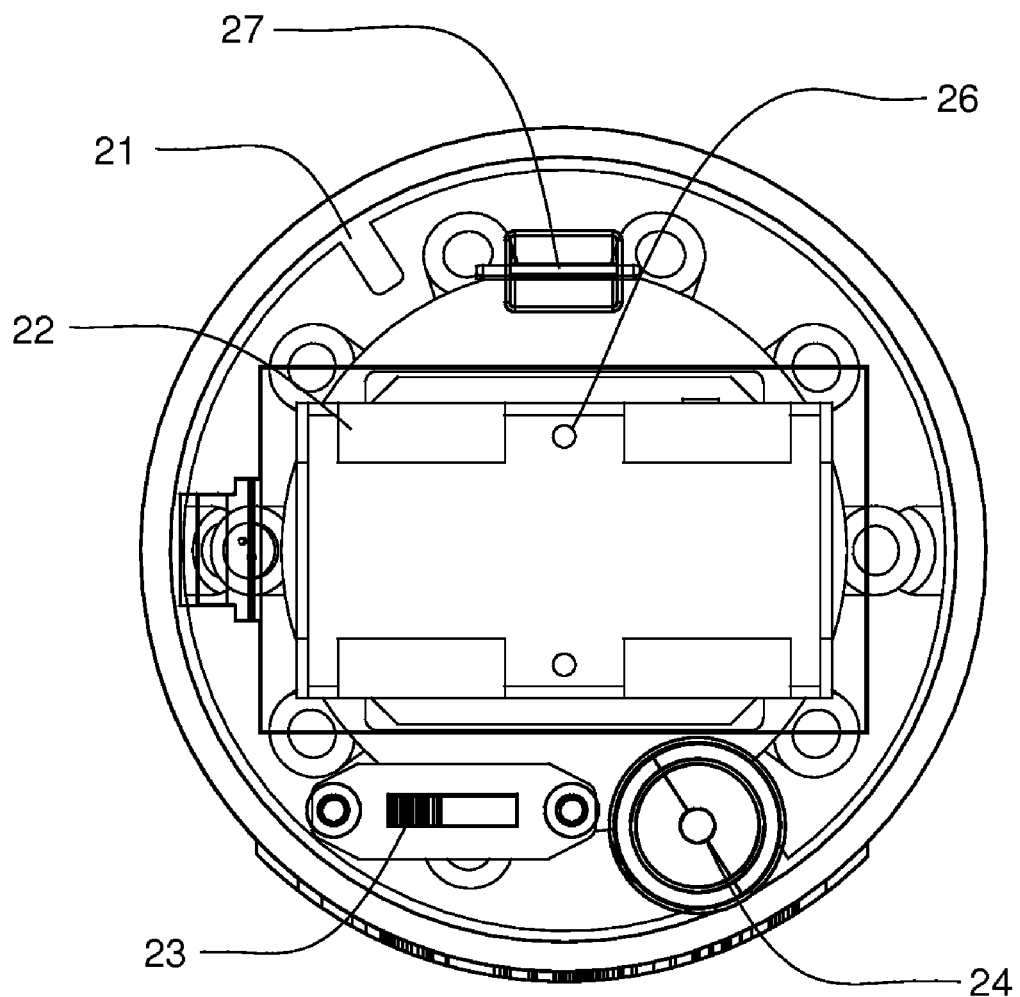
FIG. 10 is a depiction of the lens support case of the present invention, from the top.
Figure 11:
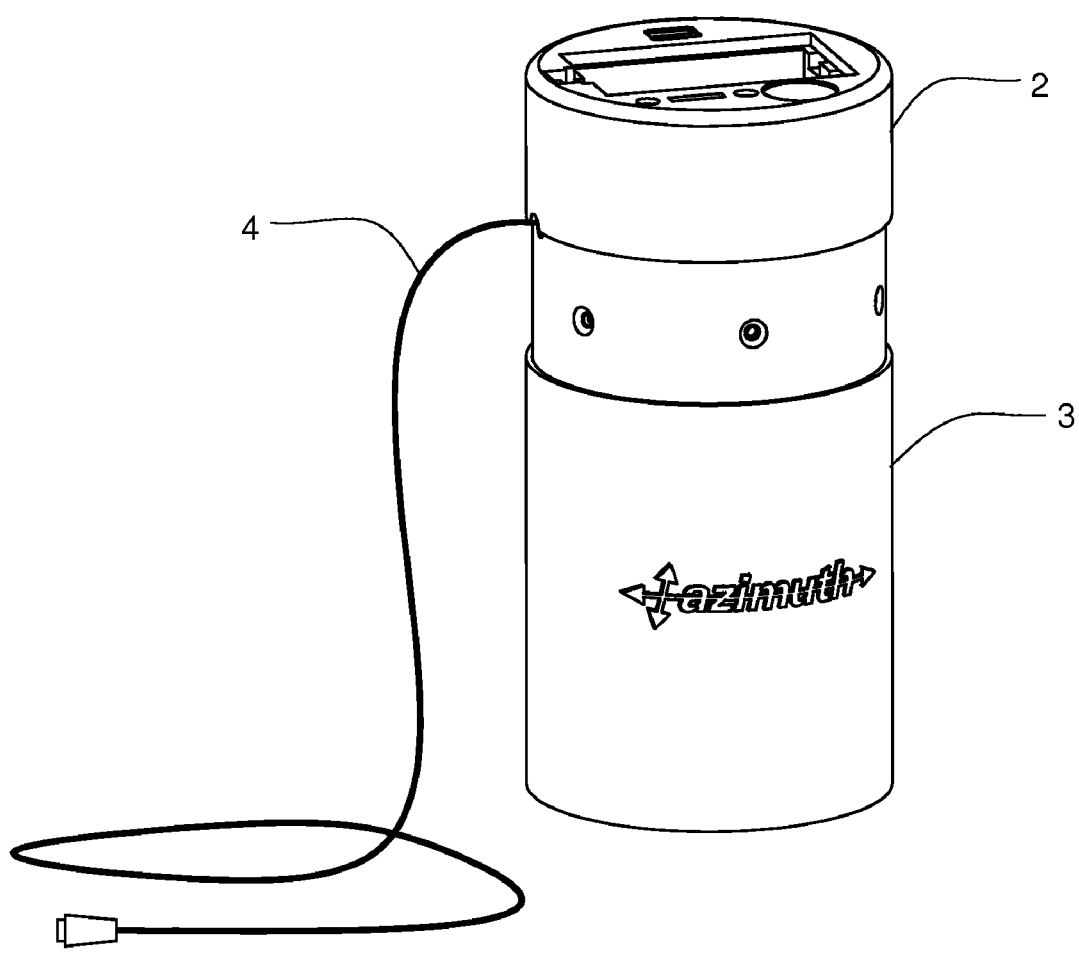
FIG. 11 is an exterior view of the casing of the present invention.
Figure 12:
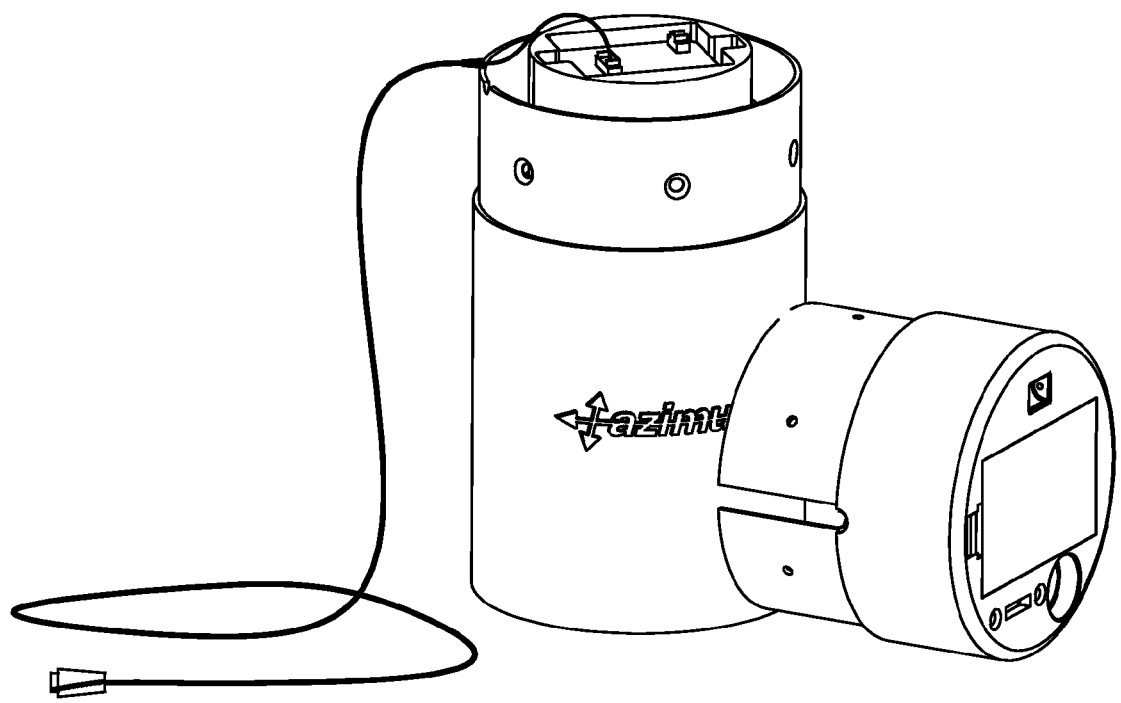
FIG. 12 is an exterior view of the present invention.
Figure 13:
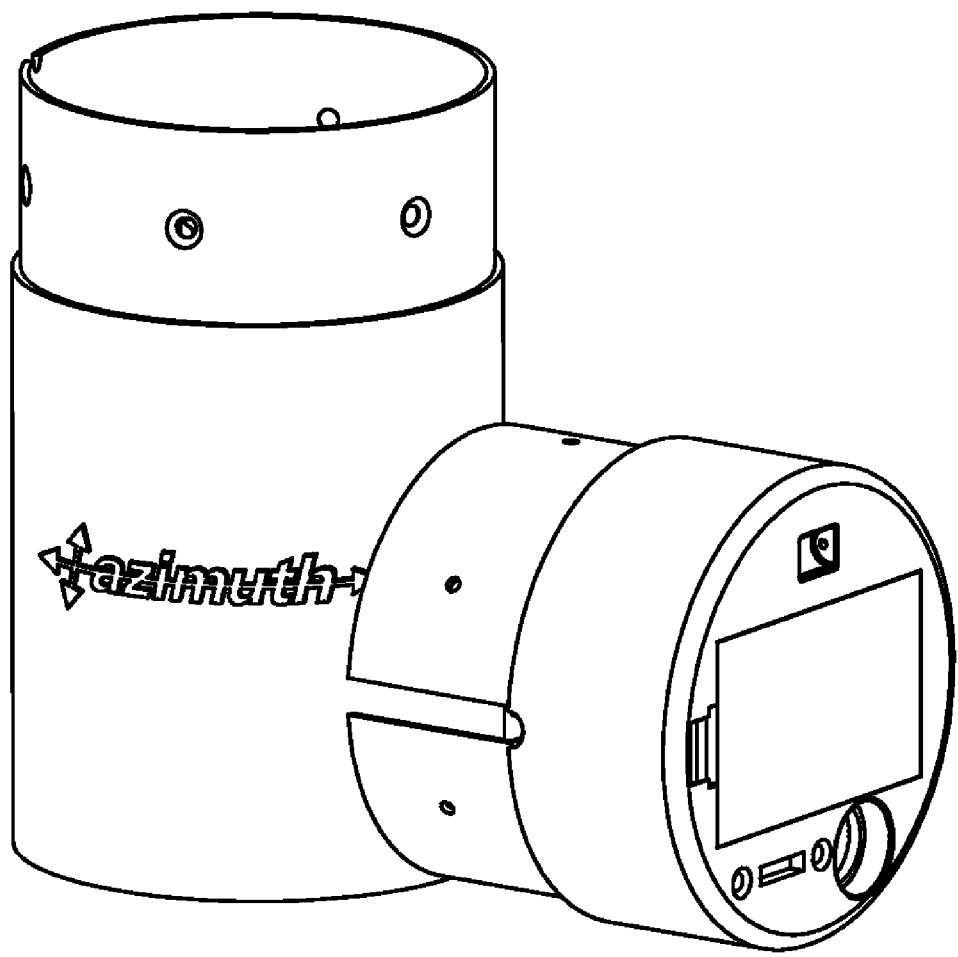
FIG. 13 is a view of the casing of the present invention.
Figure 14:
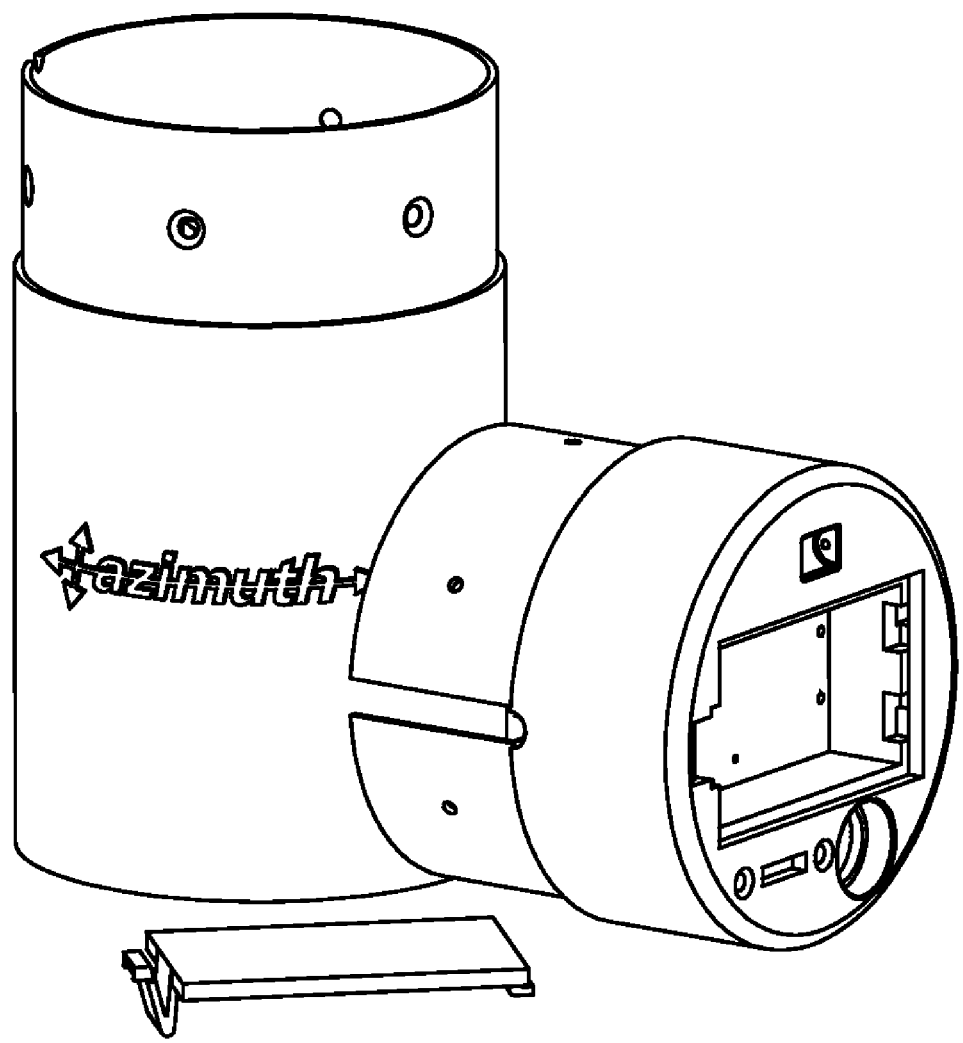
FIG. 14 is a view of the casing of the present invention.
Figure 15:
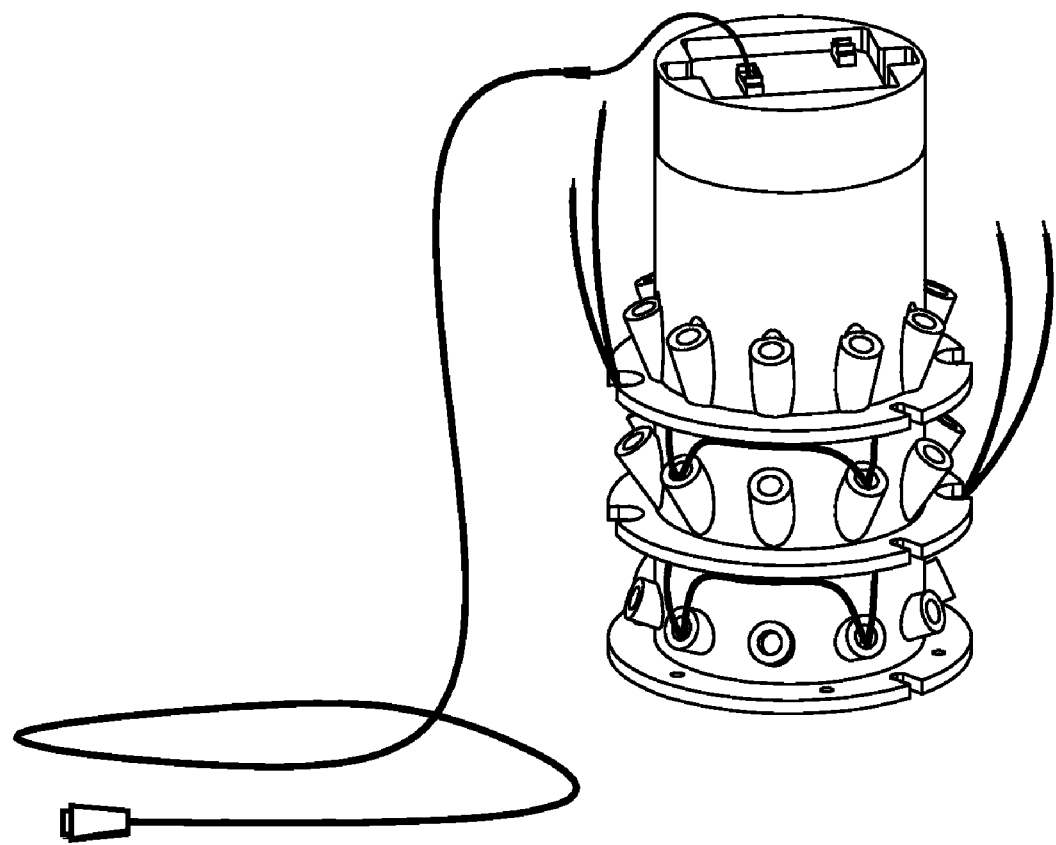
FIG. 15 is a view of the light and lens support structure of the present invention.
Figure 16:
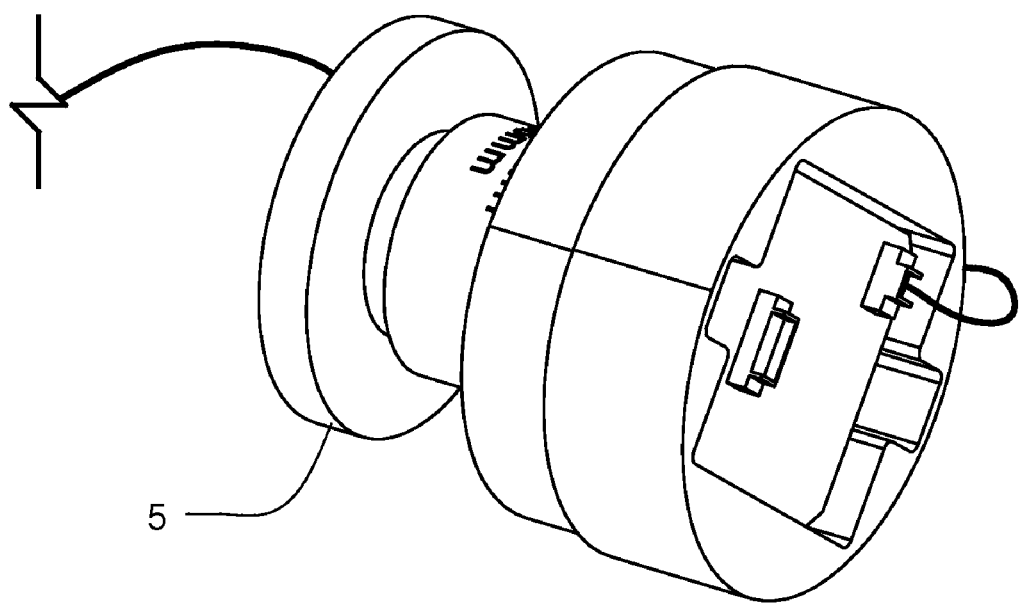
FIG. 16 is a view of the lens support structure of the present invention.
Figure 17:
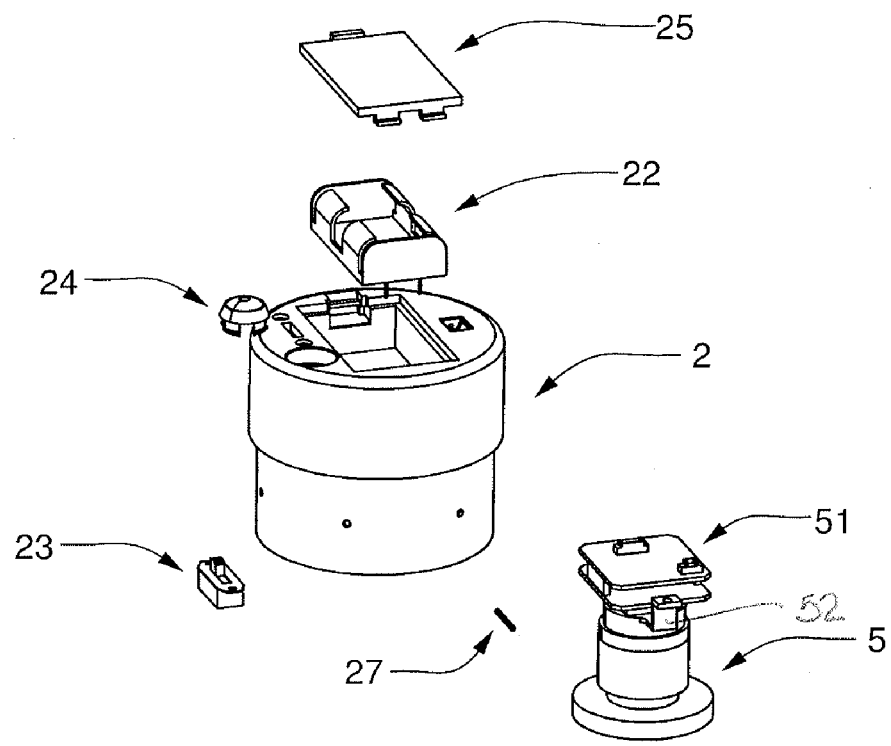
FIG. 17 is an exploded view of structural components of the present invention.
Figure 17:
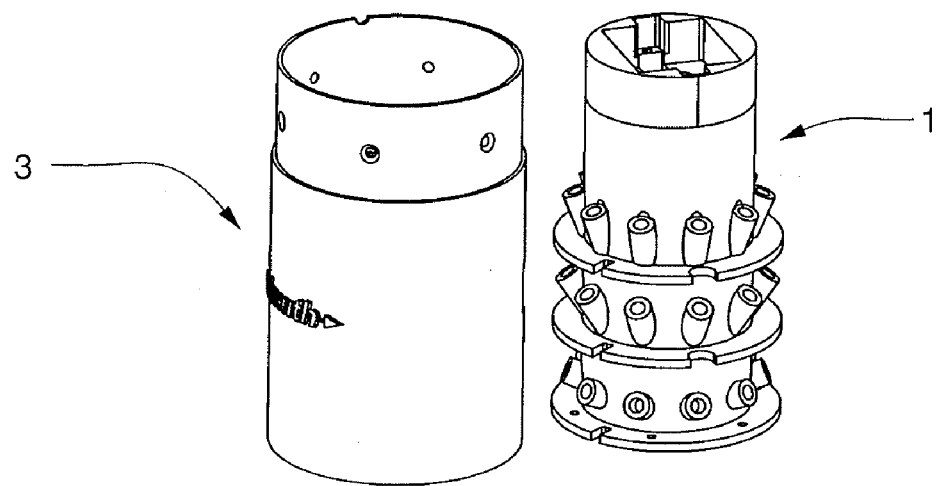
Figure 18:
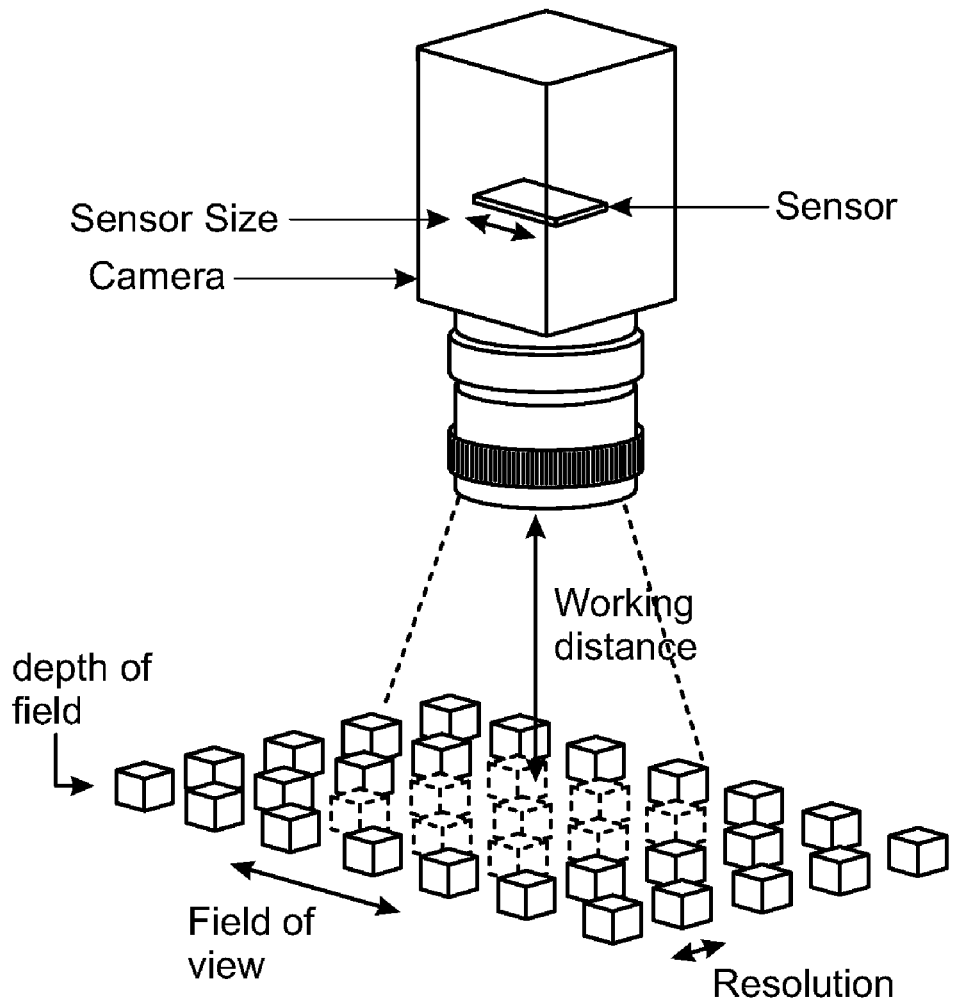
FIG. 18 is a diagram showing various components and values useful in the present invention.

Lens System. The lens system of the present invention comprises a lens 5, a support bracket 52, and a circuit board 51. In an embodiment, the lens is a single element 16 mm lens coupled with a sensor having a resolution of between 1600 and 2000 pixels (or higher), having a form factor of ⅓" CCD and a spectral response at wavelengths of 380-750 nm (for visible detection) and 365-405 nm (for UV fluorescence detection). The sensor further comprises a TWAIN interface to allow it to communicate with image processing software.

Furthermore, preferably coupled with the lens are illumination optics, including a thermo formable diffuser film, matt finish, with at least 60% transmissivity.

Image Sensors. There are two available sensor technologies solutions to image fingerprints given the present application: the CCD (Charge Coupled Device) and the CMOS (Complimentary Metal Oxide Semiconductor). Both technologies capture light from the lens, and convert it into electronic signals to image in either black and white, or color. While CCDs are presently superior image sensors, less-expensive CMOS image sensors may be suitable for use in the present invention.

Shutters and Gating. The device of the present invention further comprises a gating system (preferably pulse-width modulated) coupled with the light supply to control the amount of light delivered by the excitation (light) source. A shutter system is incorporated with the lens and sensor to control the light path through the camera lens from the fingerprint image and the emission fluorescence.

Because fluorescing light has longer wavelengths than the excitation light, a Stokes Shift phenomenon results. To overcome this phenomenon, your inventors prefer to gate the sensor, thereby allowing initiation of integration after initial excitation by the light source. Alternatively a bandpass (or bandstop) optical filter can be incorporated in front of the sensor to attenuate reflected light at 'excitation' wavelengths.

Lens Support Structure (2). The lens 5 is supported by a lens support structure 2. In current embodiments, this lens support structure 2 comprises a battery housing 22 and a battery cover 25; a three-way switch 23; a recess 15 configured to support the lens circuit board 51; and a lens aperture 16 which receives the lens into the cavity of the light support structure 1 as hereinafter described.

Light Source (28). The device of the present invention has one or more light sources 28 positioned within the cavity 14 of the light support structure, permitting illumination within the cavity and to the surface (on which a latent fingerprint is located), in different spectrums to capture the latent print in the best illumination for the chemical makeup of the print. Preferably the device of the present invention includes a plurality of light sources, including a light source supplying ultraviolet light, a light source supplying white light, and a light source supplying blue light to the cavity 14 of the light support structure. The three-way switch 23 of the lens support structure is designed and configured to control which light source (type of light) is illuminated within the cavity 14.

In some embodiments the light source provided is a string of lights, incorporated with the light support structure as hereinafter described. The light source is preferably powered by AA batteries, which are readily available worldwide.

There are presently three basic types of forensic light sources: lasers; alternate light source (ALS); and light emitting diodes (LED). Each of the three has known advantages and disadvantages in frequency covered, spectral purity, optical intensity, electrical power consumed, cost, and portability.

These light sources can be used to directly illuminate the fingerprint, with the sensor collecting the reflected light. Further, the light sources may be used in fluorescent photography, where the image material (latent oils and body salts) create their own light source by absorbing light in one wavelength band (the excitation band) and re-emitting light in a longer wavelength band (the fluorescence emission band). The sensor captures this fluorescence emission band. Fluorescence of latent fingerprints can simply occur by the fingerprint itself, or with fluorescence dyes used to dust the latent fingerprints. Much of the current latent collection research is focused in the ultra violet (UV) (220-400 nm) and in the visible blue green frequencies (400-550 nm). These are the excitation frequencies from the light source, and the camera must be able to capture the fingerprint typically at a range of about 100 nm above the emission frequency.

In the visible spectrum, the light source is preferably full color, primary component based LEDs (preferably not InGaN-active-layer coated), having a radiated angle of 80°, and a luminosity of at least 125 mcd. In the ultraviolet spectrum, the light source preferably has a peak radiated wavelength of 356-385 nm, a radiated angle of 40-120°, and optical power of about 10 mw. Preferably there are at least 8 of each light source, each type being dispersed equidistant about the circumference of the cylinder 10 of the light support structure 1, as hereinafter described.

Light Support Structure (1). The light support structure 1 comprises a cylinder 10 forming a cavity 14, and having a plurality of light ports 11, which ports are designed and configured to hold at least one type of light source hereinbefore described, allowing the bulbs of the light source to emit light within the cavity 14 of the structure 1. The ports are configured and positioned so that when in position, the lights focus on the surface on which the fingerprint is located. When assembled, the cavity 14 receives the lens 5.

In some embodiments, the light support structure 1 further comprises at least one, preferably a pair, of wiring recesses 12A, which retain the wiring of the light source(s). In some embodiments, the light support structure 1 comprises a positioning rib recess which corresponds to a rib on the exterior casing 3, as hereinafter described.

The light support structure 1 is removably affixed to the lens support structure 2 by affixation means 17, comprising in this embodiment a screw and threaded aperture. However, other means of removably affixing the structures together may be used.

Switch/Controller. A three-way switch 23 controls which light source is used for an image, and allows the user to change the same, and capture multiple images of the same print, using different light sources. Alternatively, a controller may be embedded within the system (preferably a 12 bit microcontroller operating at 16 MHz or faster, having a plurality (preferably 24) digital input/output (DIO) lines capable of sinking 20 mA or more current, a host control interface and transceivers, supporting power regulation, duty cycle control and switching circuitry).

Exterior Casing. The structure of the present invention further comprises exterior casing 3 which protects the components of the structure during use in the field. The bottom of the exterior casing preferably includes a dust cap recess 18A, finger holds 19A to permit removal of the dust cap, and recessed screw holes to permit affixation of the light support structure 1 to the bottom of the exterior casing 3.

The exterior casing 3 is designed to fit with the lens support structure 2, so that the casing can be removed, but does not easily remove so as to inadvertently separate during use. The exterior casing may have a rib 21 to cause the same to be stably secured to the light support structure 1 and the lens support structure 2.

USB Cord. The present invention is designed to connect to a portable computer by means of a USB cord 4 (preferably USB 2.0 High Speed). An aperture is incorporated into the casing to permit the USB cord to enter into the lens and connect to the circuit board 51 of the lens, allowing digital signals representing an image of latent fingerprints or similar forensic evidence to be transmitted to a computer (preferably a portable computer), allowing control of the lens magnification, and providing power from said computer to the lens. It is contemplated that the computer will have the requisite software to process multiple pictures in different spectrums.

Assembly. The device of embodiments of the present invention is assembled by placing the lens 5 within the lens support structure 2, so that the lens protrudes from the bottom of said structure, and the circuit board 51 rests on circuit board recess 15. The battery case 22 is then placed on top of the circuit board 51, and batteries are introduced therewithin. The light sources 28 are positioned within the light ports 11, so that the bulbs are located towards the cavity 14 of the cylinder 10. Finally, the lens support structure 2 is secured to the light support structure 1, and the casing is slid over the light support structure 1.

Design Example. For purposes of example, the present invention may include a 16 mm single element lens coupled with an imaging sensor having 1600*2000 pixel resolution (or higher), a form factor of about ⅓" CCD, a TWAIN interface, with a spectral response of 380-750 nm (visible) and 365-405 nm for UV fluorescence detection. The light source of this example includes visible spectrum light comprising 8 full color, primary component based (not InGaN-active-layer coated) LEDs, having a radiated angle of 80 degrees, luminosity of 125 mcd or better. The light source further comprises ultraviolet light, having a peak radiated wavelength of 365-385 nm, a radiated angle of 40-120 degrees, and having an optical power of 10 mw.

Preferably coupled with the lens are illumination optics, having a thermoformable diffuser film, with a matt finish, transmissivity of at least 60%, and polarization filters.

The embedded controller preferably comprises a 12 bit microcontroller operating at 16 MHz or faster, 24 DIO lines (min) capable of sinking 20 mA or better, a host control interface and transceivers, and supporting power regulation, duty cycle control and switching circuitry, with the host interface being a USB 2.0 high speed interface or higher.

For a ⅓" sensor, the sensor area is 4.8 mm×3.6 mm. Assuming the images to be captured are about 37 mm×28 mm, the magnification sought would be 1/7.7. Magnification can be estimated by the formula:

$$m = \text{(focal length)} / \text{(focus distance} - \text{focal length)}$$

Assuming a focus distance of 100 mm, the magnification requirement of 1/7.7 results in a focal length of 11.49 mm (well within the capabilities of the 16 mm lens). The FOV for this lens/sensor/subject combination is then determined by the formula:

$$\text{FOV(rectilinear)} = 2 * \arctan(\text{frame size} / (\text{focal length} * 2 * (m+1)))$$

If we took a look then at the diagonal FOV, the above equation yields FOV=26°

Many combinations can yield the same effective result. The idea is to use the longest possible focal length (at the compromise of light and length) that will produce a narrow FOV, to reduce the effects of perspective distortion. While one can use the progressively shorter focal lengths to capture the same field of view (and shorter camera to subject distance), the price to be paid is that distortion due to perspective increases.

In order to reduce FOV, the focal length increases and correspondingly (for the same magnification) so does the focus distance, all of which contribute to a larger device. There are a myriad of equations relating to FOV and DOF but because it is human perception we are dealing with, at the end of it all is a subjective value (a "circle of confusion"). However the guideline of 5 line-pairs-per-mm for human visual acuity is for direct observation by the naked eye. The planned resolution of 1000 dpi should yield approximately 20 line-pairs-per-mm or, in other words (for it to be useful), an expected magnification (at the final stage for the fingerprint examiner) of 4× at a viewing distance of 10-50 cm for optimal 'consumption' by the examiner.

In this example, the lens choice with a resulting FOV of 26 degrees is approximately equivalent to a 90 mm lens fitted to a 35 mm camera, where focal lengths of 70-100 mm is typically used in portraiture to minimize distortion. A roughly 30 degree FOV allows a subject to fill the frame while appearing 'correct' (the perspective is neither exaggerated or diminished).

Usage. In use, the device of the present invention is transported to a location where latent fingerprints are located; the fingerprints may be dusted with appropriate reagents, if necessary to make visible or to fluoresce. The device is then connected to a portable computer by means of the USB cord 4. The user may then remove the dust cap, if any, and place the bottom of the device directly on the surface containing the fingerprints. He selects the appropriate light source by means of the three way switch 23, and presses the light/lens power button. The lights selected then illuminate, the lens gathers and the sensor captures the image, and the digital image is transmitted by the USB cord to the computer. The user may then select another light source, and repeat the process.

We claim:

1. A portable photographic imaging system for capturing images of fingerprints, said system comprising:
   a lens to gather an image of a fingerprint,
   a sensor coupled to the lens to capture the gathered image,
   a first light source, comprising a plurality of lights and supplying ultra violet light,
   a second light source comprising a plurality of lights and supplying white light, and
   a third light source comprising a plurality of lights and supplying blue light,
   a light support structure comprising a cavity,
   a lens support structure comprising a battery housing, a three-way switch, and a lens aperture which receives the lens into the cavity of the light support structure,
   a structure having a closed top and an open bottom, an exterior surface, and an interior surface, said structure supporting the lens support structure and the light support structure, wherein the system is designed and configured so that when the open bottom of the structure is positioned on a surface having a fingerprint, one of the first, second and third light sources may be activated to illuminate the interior of the light support structure and the surface exposed with the opening of the open bottom, the lens can gather one or more images of the fingerprint, and the sensor can capture the one or more gathered images.

2. The portable photographic imaging system of claim 1, further comprising an interface to cause the system to communicate with an image processing software.

3. The portable photographic imaging system of claim 1, further comprising
   a gating system, said gating system being coupled with the light sources to control the amount of light delivered by the light sources; and
   a shutter system to control the light path through the lens, wherein the sensor is gated.

4. The portable photographic imaging system of claim 1, wherein the light support structure comprises a cylinder forming a cavity, and having a plurality of light ports that support the first, second and third light sources.

5. The portable photographic imaging system of claim 1, wherein the lens is a single element 16 mm lens and is coupled with illumination optics having a thermoformable diffuser file, with a matt finish, transmissivity of at least 60%, and polarization filters.

6. The portable photographic imaging system of claim 1, further comprising an exterior casing affixed to said structure supporting the lens support structure and the light support structure.

7. A method for capturing images of fingerprints on surfaces, said method comprising the steps of:
   (a) using a portable photographic imaging system comprising
      a lens,
      a sensor,
      a first light source supplying ultra violet light,
      a second light source supplying white light, and
      a third light source supplying blue light,
      a light support structure having a cavity,
      a lens support structure comprising a battery housing, a three-way switch and a lens aperture which receives the lens into the cavity of the light support structure,
      a structure having a closed top and an open bottom, an exterior surface and an interior surface, said structure supporting the lens support structure and the light support structure;
   (b) placing the open bottom of the imaging system directly on the surface, over the fingerprint; and
   (c) activating one of the first, second and third light sources, the lens and the sensor so that the lens gathers an image of the fingerprint and the sensor captures the image.

8. The method of claim 7, wherein the system further comprises an interface to cause the system to communicate with an image processing software.

9. The method of claim 7, wherein the system further comprises
   a gating system, said gating system being coupled with the light sources to control the amount of light delivered by the light sources; and
   a shutter system to control the light path through the lens, wherein the sensor is gated.

10. The method of claim 7, wherein the light support structure comprises a cylinder forming a cavity, and having a plurality of light ports that support the first, second and third light sources.

11. The method of claim 7, wherein the lens is a single element 16 mm lens and is coupled with illumination optics having a thermoformable diffuser file, with a matt finish, transmissivity of at least 60%, and polarization filters.

12. The method of claim 7, wherein the system further comprises an exterior casing affixed to said structure supporting the lens support structure and the light support structure.

* * * * *